US008784732B1

(12) United States Patent
Lewis et al.

(10) Patent No.: US 8,784,732 B1
(45) Date of Patent: Jul. 22, 2014

(54) AUTOCLAVE AND METHOD FOR TREATING REGULATED MEDICAL WASTE USING INJECTION OF BURSTS OF STREAM

(75) Inventors: Robert W. Lewis, Charlotte, NC (US); Timothy A. Barrett, Douglassville, PA (US)

(73) Assignee: OnSite Sterilization LLC, Pottstown, PA (US)

( * ) Notice: Subject to any disclaimer, the term of this patent is extended or adjusted under 35 U.S.C. 154(b) by 0 days.

(21) Appl. No.: 13/136,988

(22) Filed: Aug. 16, 2011

Related U.S. Application Data

(63) Continuation-in-part of application No. 11/904,417, filed on Sep. 27, 2007, now Pat. No. 8,518,340.

(51) Int. Cl.
| | |
|---|---|
| *A61L 2/08* | (2006.01) |
| *A61L 2/00* | (2006.01) |
| *A61L 2/04* | (2006.01) |
| *A61L 9/00* | (2006.01) |
| *A61L 11/00* | (2006.01) |
| *C23F 11/00* | (2006.01) |
| *A61L 2/18* | (2006.01) |
| *A61L 2/20* | (2006.01) |

(52) U.S. Cl.
USPC .................. 422/26; 422/1; 422/28; 422/33

(58) Field of Classification Search
USPC .................. 422/26, 1, 28, 33, 292, 295, 298
See application file for complete search history.

(56) References Cited

U.S. PATENT DOCUMENTS

| 2,605,969 | A  | * | 8/1952  | Sanders ..................... 236/46 R |
| 3,511,169 | A  | * | 5/1970  | Jones et al. ..................... 99/370 |
| 3,576,180 | A  | * | 4/1971  | Michel ..................... 122/406.5 |
| 3,992,984 | A  | * | 11/1976 | Treiber ......................... 99/330 |
| 5,424,046 | A  | * | 6/1995  | Smith et al. ................. 422/295 |
| 5,445,329 | A  | * | 8/1995  | Anderson ..................... 241/65 |
| 5,540,391 | A  | * | 7/1996  | Anderson ..................... 241/17 |
| 5,655,718 | A  | * | 8/1997  | Anderson ..................... 241/17 |
| 6,139,793 | A  | * | 10/2000 | Vanderwal ....................... 422/1 |
| 7,214,354 | B2 | * | 5/2007  | Ongaro ........................ 422/298 |
| 7,692,050 | B2 | * | 4/2010  | Adams et al. ............... 585/240 |
| 2003/0147771 | A1 | * | 8/2003 | Hodgins ........................ 422/26 |
| 2005/0113611 | A1 | * | 5/2005 | Adams et al. ............... 585/240 |
| 2008/0217444 | A1 | * | 9/2008 | Michalek et al. ................ 241/1 |

\* cited by examiner

*Primary Examiner* — Regina M Yoo
(74) *Attorney, Agent, or Firm* — John F. A. Earley, III; Frank J. Bonini, Jr.; Harding, Earley, Follmer & Frailey, P.C.

(57) ABSTRACT

A steam autoclave for treating Regulated Medical Waste that uses a condensate drainage system that provides for condensate drainage while the steam autoclave chamber remains pressurized during the steam treatment cycle to create pressure variations in the autoclave which are used to initiate the introduction of repeated bursts of steam into the waste during the steam treatment cycle. The repeated bursts of steam into the autoclave during the steam treatment cycle agitates the steam and waste contained in the autoclave, thereby enhancing steam penetration into the waste being treated and thereby enhancing biological kill efficacy.

18 Claims, 3 Drawing Sheets

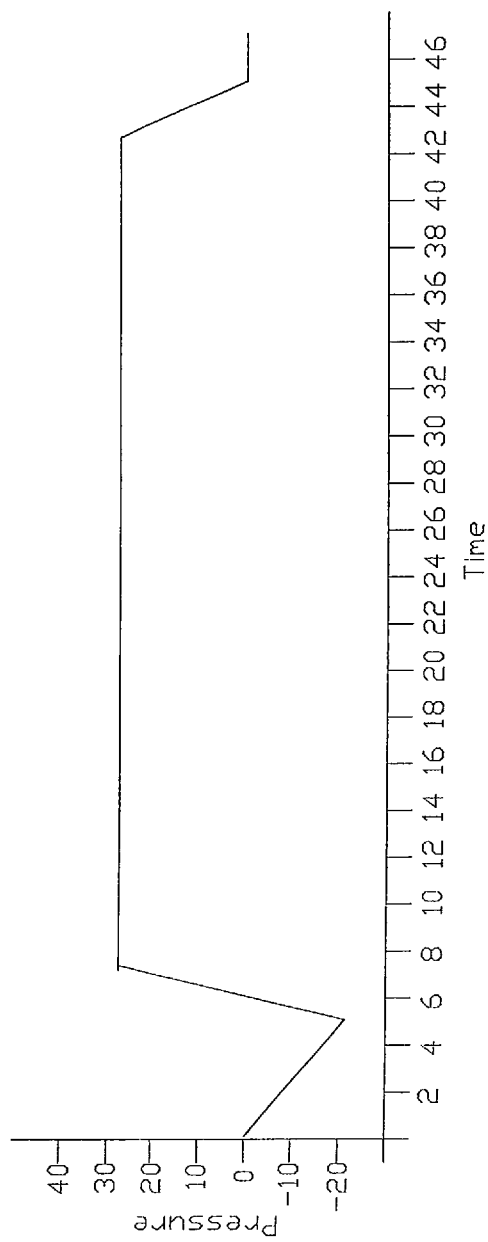
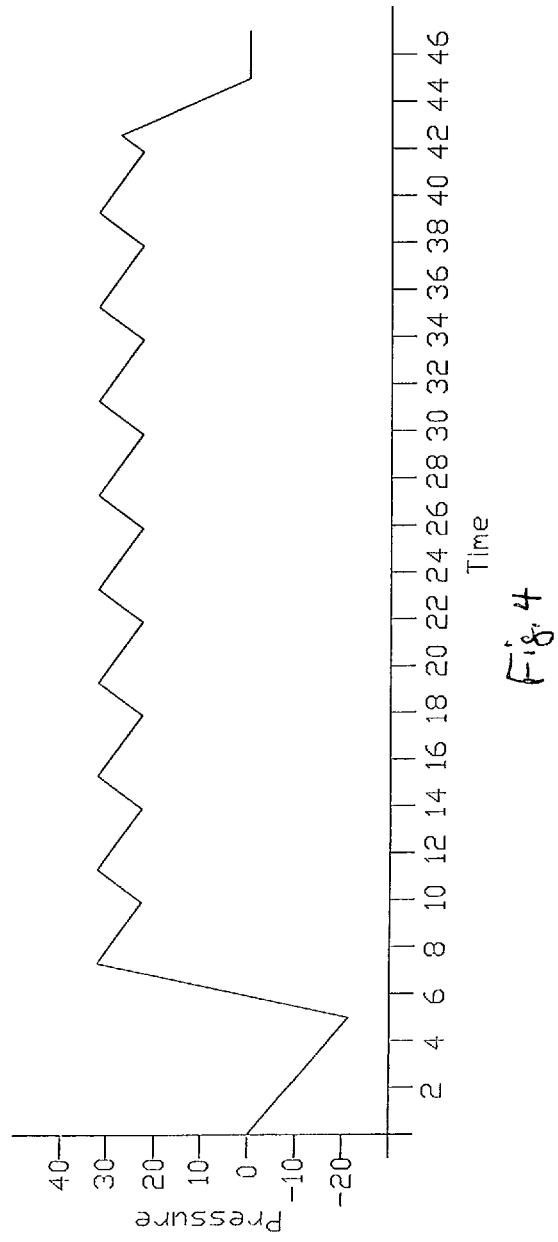

AUTOCLAVE AND METHOD FOR TREATING REGULATED MEDICAL WASTE USING INJECTION OF BURSTS OF STREAM

CROSS REFERENCE TO RELATED APPLICATION

This is a continuation-in-part application based on and claiming priority and benefit under 35 U.S.C. §120 of U.S. patent application Ser. No. 11/904,417, which was filed on Sep. 27, 2007 now U.S. Pat. No. 8,518,340 and which is incorporated herein by reference.

FIELD OF THE INVENTION

The invention relates to steam autoclaves for treating Regulated Medical Waste, and more particularly concerns a steam autoclave for treating Regulated Medical Waste that uses a condensate drainage system that provides for condensate drainage while the steam autoclave chamber remains pressurized during the steam treatment cycle to create pressure variations in the autoclave which are used to initiate the introduction of repeated bursts of steam into the waste during the steam treatment cycle. The repeated bursts of steam into the autoclave during the steam treatment cycle agitates the steam and waste contained in the autoclave, thereby enhancing steam penetration into the waste being treated and thereby enhancing biological kill efficacy.

BACKGROUND OF THE INVENTION

Containment systems, including inner and outer packaging, have significantly improved during the twenty-five (25) years since the inception of regulations governing the treatment, packaging, and transportation of Regulated Medical Waste. Containment systems for preventing liquid (e.g., blood and bodily fluids) spillage and sharps (e.g., needles, glass, scalpels, etc.) exposure for avoidance of puncture wounds have made great strides in efficacy. These systems have triggered a re-evaluation of the treatment model for autoclaves. The "desk top" laboratory autoclaves have been replaced with pressure vessels that can process more than 2,000 pounds a cycle. Where "direct impingement" of steam on the waste to obtain biological kill temperatures and a "surface contact" model were appropriate, container evolution and waste mass now dictate the concept of a "Thermal Transfer" model. Autoclaves are classified as thermal deactivation devices in relation to biological kill measurements. Accordingly, maximizing steam penetration to cause rapid rise to the needed kill temperatures is essential to optimum process success.

Air contained within the containment systems used to hold Regulated Medical Waste and within the autoclave (pressure vessel) used for treating Regulated Medical Waste acts as an insulator. Historically, after placing the Regulated Medical Waste in the autoclave (pressure vessel), a vacuum was drawn in the autoclave to remove air from the autoclave prior to treating the Regulated Medical Waste with steam in the autoclave. Following the drawing of a vacuum in the autoclave, steam injection into the autoclave was initiated to treat the Regulated Medical Waste placed in the autoclave with steam. Steam injection piping systems for injecting steam into the autoclave generally included in series along the piping from the main steam line to the autoclave a manual isolation valve, followed by an automated control valve, followed by a steam pressure reducer for lowering the facility's main steam pressure to the lower autoclave operating pressure. Following the pre-treatment vacuum and the initial injection of steam into the autoclave through the steam injection piping system, a static head (constant pressure) was maintained in the autoclave until the completion of the steam treatment cycle. The static head (constant pressure) was maintained in the autoclave by having the steam pressure reducer in line with the manual isolation valve and the automatic control valve, and having the manual isolation valve and the automated control valve open throughout the steam treatment cycle, the injection of new steam, and the thermal energy contained therein, into the autoclave via the steam injection piping system being dependent on the condensation rate in the autoclave during the steam treatment cycle. After the steam treatment cycle and cessation of steam injection, a post treatment cycle vacuum was drawn to flash off condensation.

Our research has determined that autoclaves (pressure vessels) operating as described in the previous paragraph do not provide consistent biological kill. The variations in mass, liquid quantities, porosity, and containment systems are not answered by a one single, set treatment cycle unless that cycle assumes the combined maximums in weight, liquid content, porosity, and containment system strength associated with the waste stream typical of that specific facility. Multiple data inputs are required to vary an autoclave's "residence time" (the time duration at or above the minimum biological kill temperature stipulated by regulations) to respond to these parametric variations. Robert W. Lewis' U.S. Pat. Nos. 6,867,393 and 7,815,851, which are incorporated herein by reference, and Robert W. Lewis' U.S. patent application Ser. No. 12/924,438, which also is incorporated herein by reference, disclose improvements relating to the treatment of Regulated Medical Waste to enhance the efficacy of such treatment, such as:

(a) varying process times, including residence time that the waste to be sterilized is exposed to steam in the autoclave, process temperatures, and process pressures, including vacuum for negative pressure and steam injection for positive pressure, to predetermined settings (determined empirically by testing the facility's waste stream) that correlate to the waste character profile (e.g., "bagged waste", "laboratory waste", or "suction canister waste") of the waste to be treated and to the weight (mass) of the waste to be treated, and (b) enhancing steam penetration and containment system disruption by using multiple vacuum/steam injection pulses.

Continuous condensation removal, as detailed in our U.S. patent application Ser. No. 11/904,417, which is incorporated herein by reference, increases autoclave efficacy by enhancing uniform biological kill throughout an autoclave.

SUMMARY OF THE INVENTION

It is an object of the invention to further enhance the efficacy of treating Regulated Medical Waste in a steam autoclave.

Further, it is an object of the invention to enhance steam penetration into the Regulated Medical Waste being treated in a Regulated Medical Waste autoclave.

These and other objects are accomplished by our new invention which is set out below. In accordance with our invention, the penetration of steam into the Regulated Medical Waste during treatment in the autoclave is enhanced by agitating the Regulated Medical Waste during the steam treatment cycle by injecting bursts of steam into the Regulated Medical Waste. In accordance with a preferred embodiment of our invention, the valve system for the steam injection piping system is rearranged from its historical arrangement to an arrangement that has in series along the piping from the main steam line to the autoclave the manual isolation valve, followed by the steam pressure reducer, followed by an automated control valve whose opening and closing during the steam treatment cycle is defined by pressure set points for pressure in the autoclave. In accordance with our invention, the removal of condensation formed in the autoclave continuously during the steam treatment cycles is used to create pressure variations in the autoclave which are used to initiate the introduction of repeated bursts of steam into the waste during the steam treatment cycle. The repeated bursts of steam into the autoclave during the steam treatment cycle agitates the steam and waste contained in the autoclave, thereby enhancing steam penetration into the waste being treated and thereby enhancing biological kill efficacy.

BRIEF DESCRIPTION OF THE DRAWINGS

FIG. 3 is a graph illustrating pressure levels in the sterilization chamber 15 during the operation of the steam autoclave 11, in which the steam feed line (first piping 17) to the sterilization chamber 15 is at a constant feed pressure and the steam feed line (first piping 17) is kept open during the operation of the steam autoclave 11 during the steam treatment cycle.

FIG. 4 is a graph illustrating pressure levels in the sterilization chamber 15 during the operation of the steam autoclave 11, in which the steam feed line (first piping 17) to the sterilization chamber 15 is at a constant feed pressure, but the steam feed line (first piping 17) is repeatedly opened and closed in accordance with our invention during the operation of the steam autoclave 11 during the steam treatment cycle, resulting in bursts of steam repeatedly entering into the sterilization chamber 15 during the steam treatment cycle.

DETAILED DESCRIPTION

Figure 1:
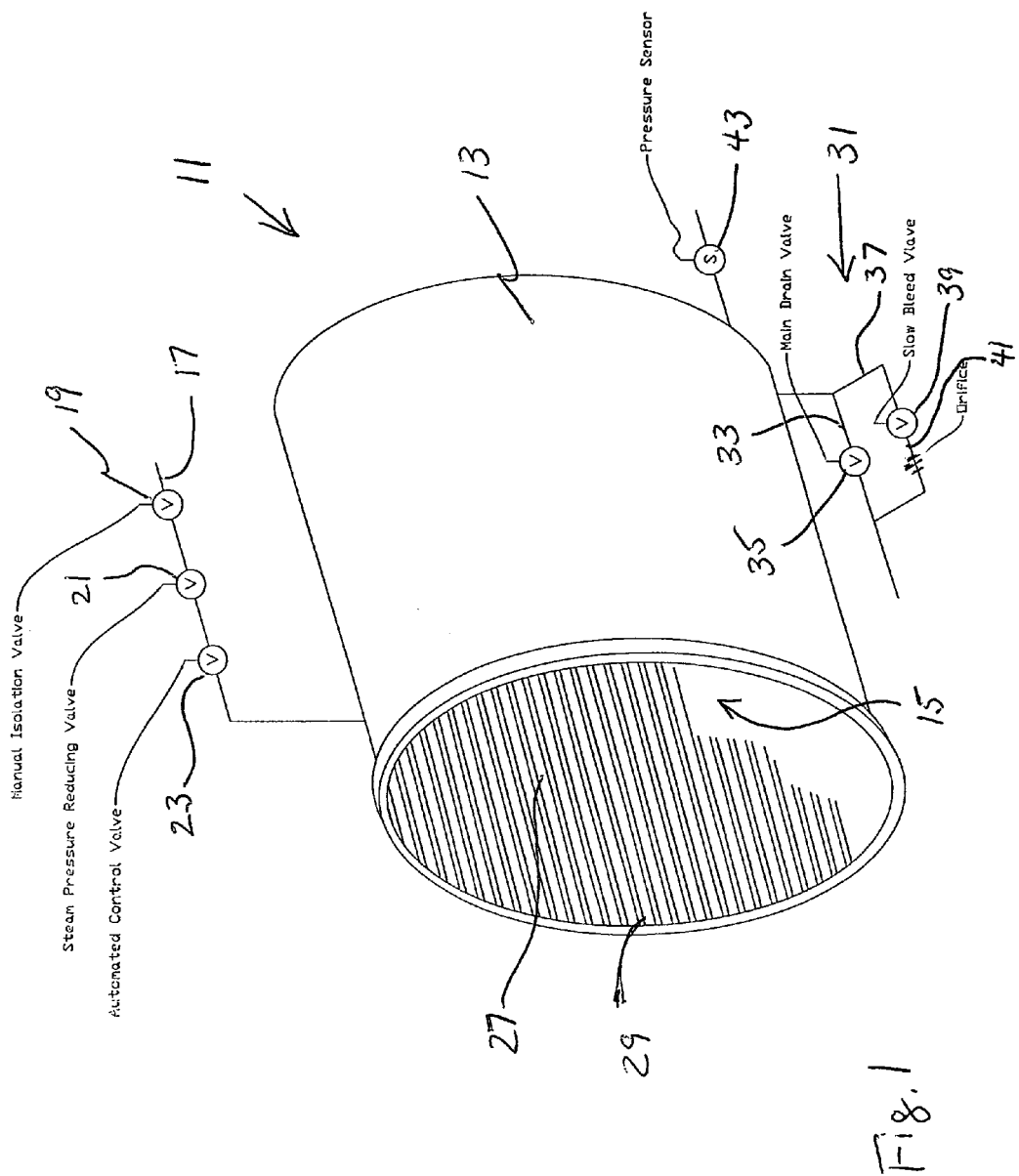
FIG. 1 is a schematic drawing illustrating a steam autoclave 11 constructed in accordance with the invention.
Figure 2:
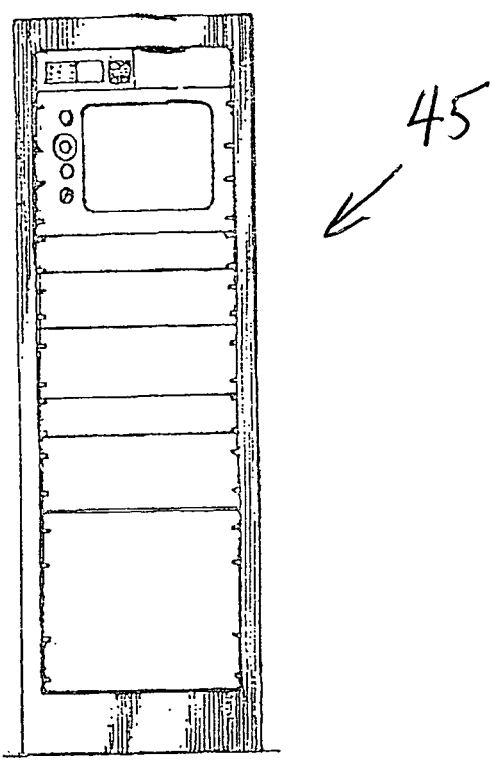
FIG. 2 is a view in front elevation showing a controller (e.g., a programmable logic controller) 45 for the steam autoclave 11.

Turning to the drawings, there is shown in FIG. 1 a preferred embodiment of our inventive steam autoclave 11 for treating (e.g., sterilizing) material and objects such as Regulated Medical Waste. The steam autoclave 11 comprises a pressure vessel 13 having a sterilization chamber 15 formed therein. The steam autoclave 11 also has a steam injection piping system that includes a first piping 17 to supply steam from a steam source (e.g., a main steam line) to the sterilization chamber 15. The steam injection piping system also includes, preferably in series, along the first piping 17 a manual isolation valve (preferably a manual ball valve) 19 as a safety feature, followed by a steam pressure reducer 21 for lowering the pressure level of the steam from the steam source (e.g., the main steam line that feeds steam to the first piping 17) to a lower operating pressure (e.g., the pressure selected to use in the operation of the steam autoclave 11), followed by an automated control valve 23 whose opening and closing during a steam treatment cycle of the steam autoclave 11 is set by selected pressure levels (selected pressure set points) for pressure in the sterilization chamber 15 of the steam autoclave 11.

The steam autoclave 11 also is provided with second piping in communication with the sterilization chamber 15 through which steam may be evacuated from the sterilization chamber 15, a vacuum pump (when desired) provided along the second piping for evacuating the sterilization chamber 15 when desired during the treatment process, and a valve (preferably an electromagnetic solenoid activated valve) provided along a vent portion of the second piping used for venting the steam sterilization chamber 15 to atmosphere. To simplify FIG. 1, standard component parts of steam autoclaves, such as the above-mentioned second piping, vacuum pump when desired, vent portion of the second piping, and the valve along the vent portion of the second piping, are not shown.

The sterilization chamber 15 has an interior 27 where steam treatment (e.g., sterilization) takes place. The sterilization chamber 15 has an opening 29 through which access to the interior 27 of the sterilization chamber 15 is obtained, and the sterilization chamber 15 has a door (not shown) mounted at the opening 29 for sealingly closing the opening 29 against both pressure and vacuum when closed. The door preferably is a full opening hinged door that provides unobstructed access to the sterilization chamber 15 when the door is fully opened. The door preferably is equipped with an automatic latching mechanism to seal the door against both pressure and vacuum. Also, the door preferably is equipped with safety interlocks to prevent opening the door until safe pressure and temperature conditions are restored.

A condensate drainage system 31 is provided for draining condensate from the sterilization chamber 15 of the steam autoclave 11. Preferably, as shown in FIG. 1, the condensate drainage system 31 includes a main drain line 33, which is in fluid communication with and extends downwardly from a lower (preferably the lowest) end portion of the bottom wall of the sterilization chamber 15, and through which condensate in the sterilization chamber 15 is drained. A main drain valve 35 preferably is mounted in the main drain line 33 for opening the main drain line 33 when desired to drain condensate from the sterilization chamber 15. An auxiliary drain line 37, preferably being in communication with the main drain line 33, also is provided through which condensate in the sterilization chamber 15 is bled (drained) when desired. Preferably, an auxiliary drain valve 39 is mounted in the auxiliary drain line 37 for opening the auxiliary drain line 37 when desired to drain condensate from the sterilization chamber 15.

The auxiliary drain line 37 has a conduit or passageway 41 extending therethrough defining a path for condensate to move through the auxiliary drain line 37. At least a portion of the conduit 41 has a cross-section sized to permit effective draining of condensate (that is, sized to effectively drain condensate) through the conduit 41 while the sterilization chamber 15 is pressurized without the occurrence of substantial loss of steam pressure in the sterilization chamber 15. Preferably, the cross-section of the at least a portion of the conduit 41 is in a range of one sixteenth of an inch to one quarter of an inch.

The conduit 41 of the auxiliary drain line 37 may have a cross-section that is constant along the entire length of the auxiliary drain line 37. Alternatively, the conduit 41 may have a restriction formed in it to create a section or portion in the conduit 41 that has a passageway cross-section that is sufficiently sized to permit effective draining of the condensate (that is, sized to effectively drain the condensate) through the conduit 41 while the sterilization chamber 15 is pressurized without the occurrence of substantial loss of steam pressure in the sterilization chamber 15. Also, alternatively, the conduit 41 may be provided with an orifice plate having and orifice sized to permit effective draining of condensate (that is, sized to effectively drain condensate) through the conduit 41 while the sterilization chamber 15 is pressurized without substantial loss of steam pressure in the sterilization chamber 15.

While it is preferred to have the auxiliary drain line 37 in direct communication with the main drain line 33 as illustrated in FIG. 1, the auxiliary drain line 37 may extend directly from the sterilization chamber 15 (preferably from a lower end portion of the bottom wall of the sterilization chamber 15), rather than extending from the main drain line 33.

Preferably, a sensor 43 is provided, positioned in the sterilization chamber 15 for sensing a pressure drop during condensate draining while the sterilization chamber 15 is pressurized and for initiating insertion of additional pressurized steam into the sterilization chamber 15 as needed to maintain adequate steam pressure in the sterilization chamber 15.

During operation of the steam autoclave 11, condensate formed in the sterilization chamber 15 may be drained from the sterilization chamber 15 as desired while the sterilization chamber 15 is pressurized by opening the auxiliary drain line valve 37, thereby permitting condensate to flow from (that is, permitting condensate to be bleed from) the sterilization chamber 15 through the auxiliary drain line 37. Due to the sizing of the cross-section in at least a portion of the conduit 41 being sized to permit effective draining of condensate (that is, sized to effectively drain condensate) through the conduit 41 while the sterilization chamber 15 is pressurized without substantial loss of steam pressure in the sterilization chamber 15, condensate may be drained from the sterilization chamber 15 while the sterilization chamber 15 is pressurized without a substantial loss of steam pressure in the sterilization chamber 15 occurring. In the preferred embodiment of the invention illustrated in FIG. 1, during operation of the steam autoclave 11, with the main drain valve 35 in a closed position and the auxiliary drain valve 39 in an opened position, condensate flows from the sterilization chamber 15 into a portion of the main drain line 33 that is upstream of the main drain valve 35 and then into and through the auxiliary drain line 37 to drain (bled) condensate from the sterilization chamber 15 while the sterilization chamber 15 is pressurized without substantial loss of steam pressure in the sterilization chamber 15. If the steam autoclave 11 is configured to have the auxiliary drain line 37 extend directly from the sterilization chamber 15 rather than extending from the main drain line 33, during operation of an autoclave so configured, with the main drain valve 35 in a closed position and the auxiliary drain valve 39 in an opened position, condensate flows from the sterilization chamber 15 directly into and through the auxiliary drain line 37 to drain (bled) condensate from the sterilization chamber 15 while the sterilization chamber 15 is pressurized without substantial loss of steam pressure in the sterilization chamber 15.

Preferably, the sterilization chamber 15 is provided with the sensor 43 which senses any pressure drop in the sterilization chamber 15 during condensate draining while the sterilization chamber 15 is pressurized and initializes insertion of additional pressurized steam into the sterilization chamber 15 as needed to maintain adequate steam pressure in the sterilization chamber 15. Preferably, a controller (e.g., a programmable logic controller) 45 is provided with the steam autoclave 11 to manage the control functions and system interlocks. The controller 45 preferably controls the steam valves, vent valves, drain valves 35 and 39, and vacuum pump, as well as controlling the insertion of additional pressurized steam from the steam feed line (first piping 17) into the sterilization chamber 15 as needed to maintain adequate steam pressure in the sterilization chamber 15 in response to a drop in steam pressure sensed by sensor 43.

Preferably, the autoclave systems and methods, such as those set out in detail in Robert W. Lewis' U.S. Pat. Nos. 6,867,393 and 7,815,851, which are incorporated herein by reference, and Robert W. Lewis' U.S. patent application Ser. No. 12/924,438, which is incorporated herein by reference, may be used in our invention, but with the modification disclosed herein. For instance, in accordance with our invention, in addition to treating Regulated Medical Waste in an autoclave by using the steps of (a) placing Regulated Medical Waste to be treated into a sterilization chamber of the autoclave, (b) removing the air from the sterilization chamber, (c) feeding steam into the sterilization chamber until a selected first pressure level is reached and then discontinuing feeding steam into the sterilization chamber when the selected first pressure level is reached, (d) heating the sterilization chamber and the Regulated Medical Waste contained therein with the steam for a desired period of time, (e) drawing a vacuum in the sterilization chamber, (f) feeding steam into the sterilization chamber again until a selected first pressure level is reached and then discontinuing feeding steam into the sterilization chamber when the selected first pressure level is reached, (g) heating the sterilization chamber and the Regulated Medical Waste contained therein again for a desired period of time, and (h) drawing a vacuum in the sterilization chamber again, the following step is used to inject a blast of steam into the sterilization chamber to agitate the steam and waste contained in the sterilization chamber of the steam autoclave during a steam treatment cycle, thereby enhancing steam penetration into the waste being treated and thereby enhancing biological kill efficacy: (i) during either or both of steps (d) and (g) set out above in this paragraph, draining condensate from the sterilization chamber, sensing a pressure drop in the sterilization chamber caused by condensate draining while the sterilization chamber is pressurized, and automatically feeding additional steam into the sterilization chamber when the pressure drop reaches a second selected pressure level and continuing to do so until the first selected pressure level in the sterilization chamber is reached again. Step (b) set out above in this paragraph may be accomplished by drawing vacuum in the sterilization chamber, or the combination of steps (b) and (c) set out above in this paragraph may be accomplished by displacing the air in the sterilization chamber with steam, such as by gravity feeding steam into the sterilization chamber to displace the air in the sterilization chamber therewith. Repeated blasts of steam may be injected into the sterilization chamber by repeating step (i) set out above in this paragraph each time the pressure level in the sterilization chamber again drops to the second selected pressure level during either or both steps (d) and (g) set out above in this paragraph.

Throughout each steam treatment cycle during the operation of the steam autoclave 11 in accordance with a preferred embodiment of the invention, bursts of steam are automatically injected into the sterilization chamber 15 from the steam feed line (first piping 17). This is accomplished as follows. First, the steam treatment cycle is commenced by feeding steam into the sterilization chamber 15 until a first selected pressure level in the sterilization chamber 15 is reached. When the first selected pressure level in the sterilization chamber is reached, the feeding of steam into the sterilization chamber 15 from the steam feed line (first piping 17) is automatically discontinued by initiating a signal from the sensor 43 positioned in the sterilization chamber 15 whose pressure in the sterilization chamber 15 reaches the first selected pressure level to cause the automated control valve 23 provided on the steam feed line (first piping 17) for feeding steam into the sterilization chamber 15 to close. The steam autoclave 11 is configured such that the programmable logic controller 45 receives signals from the sensor 43 reflecting pressure levels in the sterilization chamber 15 sensed by the sensor 43 throughout the operation of the steam autoclave 11, and when the programmable logic controller 45 receives a signal from the sensor 43 indicating that the first selected pressure level (first pressure set point) (which has been selected as the high end pressure level to be used during the steam treatment cycle, and which has been inputted into the programmable logic controller 45) has been reached, the programmable logic controller 45 signals the automated control valve 23 to close. Throughout the steam treatment cycle, condensate formed in the sterilization chamber 15 is continuously removed (bled off) from the sterilization chamber 15 via the auxiliary drain line 37, which causes a pressure drop to occur in the sterilization chamber 15. Each time the sensor 43 senses that the pressure level in the sterilization chamber 15 has dropped to a second selected pressure level (second pressure set point) (which has been selected as the low end pressure level to be used during the steam treatment cycle, and which as been inputted into the programmable logic controller 45), the programmable logic controller 45 receives a signal from the sensor 43 reflecting that the pressure level in the sterilization chamber 15 has reached the second selected pressure level and in response thereto signals the automated control valve 23 to open, thereby automatically feeding a blast of steam into the sterilization chamber 15 until the programmable logic sensor 45 receives a signal from the sensor 43 reflecting that the pressure level in the sterilization chamber 15 has again risen to the first selected pressure level and in response thereto signals the automated control valve 23 to close.

Accordingly, throughout the steam treatment cycle, a blast of stem is injected from the steam feed line (first piping 17) each time the automated control valve 23 is opened in response to the pressure in the sterilization chamber 15 dropping to the second selected pressure level due to draining condensate from the sterilization chamber 15 via the auxiliary drain line 37 during the steam treatment cycle. This is reflected in FIG. 4, which shows a pressure versus time graph for an example autoclave treatment of Regulated Medical Waste chosen for illustrative purposes, in which the first selected pressure level (the first pressure set point) during the steam treatment cycle is 30 psig and the second selected pressure level (the second pressure set point) during the steam treatment cycle is 22 psig. During the example autoclave treatment, each time the pressure level in the sterilization chamber 15 reaches the second selected pressure level (second pressure set point) (22 psig in this example) during the steam treatment cycle, a blast of steam is automatically injected into the sterilization chamber 15 in accordance with the invention by automatically opening the automated control valve 23 in response to the pressure level in the sterilization chamber 15 reaching the second selected pressure level (second pressure set point) (22 psig in this example), thereby causing the pressure level in the sterilization chamber 15 to rise until the pressure level in the sterilization chamber 15 reaches the first selected pressure level (first pressure set point) (30 psig in this example), which results in automatically closing the automated control valve 23 in response to the pressure level in the sterilization chamber 15 reaching the first selected pressure level (first pressure set point) (30 psig in this example). In the example treatment reflected in FIG. 4, the steam feed line (first piping 17) to the sterilization chamber 15 is at a constant feed pressure (30 psig in this example), but the steam feed line (first piping 17) is repeatedly opened and closed in accordance with our invention during the operation of the steam autoclave 11 during the steam treatment cycle, resulting in bursts of steam repeatedly entering into the sterilization chamber 15 during the steam treatment cycle.

In contrast to FIG. 4, FIG. 3 shows a pressure versus time graph for another example autoclave treatment of Regulated Medical Waste, in which the steam feed line (first piping 17) to the sterilization chamber 15 is at a constant feed pressure (30 prig in this example) and the steam feed line (first piping 17) is kept open during the operation of the steam autoclave 11 during the steam treatment cycle. In this example treatment, any loss in pressure due to the auxiliary drain line 37 being open to permit condensate drainage while the sterilization chamber 15 is pressurized is compensated for due to the constant feed pressure from the steam feed line (first piping 17) since, in contrast to the example treatment reflected in FIG. 4, the steam feed line (first piping 17) remains open throughout the steam treatment cycle. Accordingly, the sensor 43 may be omitted when the steam feed line (first piping 17) to the sterilization chamber 15 is at a constant feed pressure and the steam feed line (first piping 17) is kept open during the operation of the steam autoclave 11.

The invention claimed is:

1. A method of treating Regulated Medical Waste in an autoclave for treating Regulated Medical Waste, comprising the steps of
   (a) placing Regulated Medical Waste to be treated into a sterilization chamber of the autoclave,
   (b) removing air from the sterilization chamber,
   (c) feeding steam into the sterilization chamber until a selected first pressure level is reached and then discontinuing feeding the steam into the sterilization chamber when the selected first pressure level is reached,
   (d) heating the sterilization chamber and the Regulated Medical Waste contained therein with the steam for a desired period of time,
   (e) drawing a vacuum in the sterilization chamber,
   (f) feeding steam into the sterilization chamber again until the selected first pressure level is reached and then discontinuing feeding steam into the sterilization chamber when the selected first pressure level is reached,
   (g) heating the sterilization chamber and the Regulated Medical Waste contained therein again for a desired period of time,
   (h) drawing a vacuum in the sterilization chamber again, and
   (i) during either or both of steps (d) and (g), draining condensate from the sterilization chamber, sensing a pressure drop in the sterilization chamber caused by the condensate draining while the sterilization chamber is pressurized, and automatically feeding additional steam into the sterilization chamber when the pressure drop reaches a second selected pressure level and continuing to do so until the selected first pressure level in the sterilization chamber is reached again.

2. The method of claim 1,
   upon completion of step (i), further including the steps of
   (j) automatically discontinuing feeding steam into the sterilization chamber when the selected first pressure level in the sterilization chamber is reached,
   (k) draining the condensate from the sterilization chamber,
   (l) sensing a pressure drop in the sterilization chamber caused by the condensate draining while the sterilization chamber is pressurized, and
   (m) automatically feeding additional steam into the sterilization chamber when the pressure drop reaches a second selected pressure level and continuing to do so until the selected first pressure level in the sterilization chamber is reached again.

3. The method of claim 2, upon completion of steps (j) to (m), repeating steps (j) to (m) when the selected first pressure level is reached in the sterilization chamber again.

4. The method of claim 2, upon completion of steps (j) to (m), repeating steps (j) to (m) each time the selected first pressure level is reached in the sterilization chamber.

5. The method of claim 1, step (b) being accomplished by drawing a vacuum in the sterilization chamber.

6. The method of claim 1, steps (b) and (c) being accomplished by displacing the air in the sterilization chamber with steam.

7. The method of claim 1,
the sterilization chamber having a condensate drain line having a conduit extending therethrough defining a path for condensate to move through the condensate drain line, and the condensate drain line having means formed thereon along at least a portion of the conduit extending therethrough for permitting effective draining of the condensate through the conduit while the sterilization chamber is pressurized without substantial loss of steam pressure in the sterilization chamber, wherein the draining step comprises draining the condensate from the sterilization chamber through the conduit of the condensate drain line.

8. The method of claim 7,
said means including an orifice plate provided on the conduit having an orifice sized to permit effective draining of the condensate through the conduit while the sterilization chamber is pressurized without substantial loss of steam pressure in the sterilization chamber.

9. The method of claim 7,
said means including a restriction formed on at least the portion of the conduit creating a cross-section thereat sized to effectively drain the condensate through the conduit while the sterilization chamber is pressurized without substantial loss of steam pressure in the sterilization chamber.

10. The method of claim 7,
said means including a cross-section of the at least the portion of the conduit being in a range of one sixteenth of an inch to one quarter of an inch.

11. A method of treating Regulated Medical Waste with steam in a steam autoclave, comprising the steps of
(a) commencing a steam treatment cycle for treating Regulated Medical Waste by feeding steam into a sterilization chamber of the steam autoclave into which Regulated Medical Waste to be treated has been placed until a first selected pressure level in the sterilization chamber is reached,
(b) automatically discontinuing feeding steam into the sterilization chamber when the first selected pressure level in the sterilization chamber is reached,
(c) heating the sterilization chamber and the Regulated Medical Waste contained therein with the steam until the steam treatment cycle is completed,
(d) draining condensate from the sterilization chamber during the steam treatment cycle while the sterilization chamber is pressurized,
(e) sensing during the steam treatment cycle a pressure drop in the sterilization chamber caused by the condensate draining while the sterilization chamber is pressurized during the steam treatment cycle, and
(f) automatically feeding additional steam into the sterilization chamber during the steam treatment cycle in response to when the pressure drop caused by the condensate draining while the sterilization chamber is pressurized during the steam treatment cycle reaches a second selected pressure level and continuing to do so during the steam treatment cycle until the first selected pressure level in the sterilization chamber is reached again,
the sterilization chamber having a condensate drain line having a conduit extending therethrough defining a path for condensate to move through the condensate drain line, and the condensate drain line having means formed thereon along at least a portion of the conduit extending therethrough for permitting effective draining of condensate through the conduit while the sterilization chamber is pressurized without substantial loss of steam pressure in the sterilization chamber, wherein the draining step comprises draining condensate from the sterilization chamber through the conduit of the condensate drain line.

12. The method of claim 11, further including
upon completion of steps (a) to (f), repeating steps (b) to (f) when the first selected pressure level is reached again in the sterilization chamber during the steam treatment cycle.

13. The method of claim 11, further including
upon completion of steps (a) to (f), repeating steps (b) to (f) each time the first selected pressure level is reached in the sterilization chamber during the steam treatment cycle.

14. The method of claim 11,
the step of discontinuing feeding steam into the sterilization chamber being accomplished by initiating a signal from a sensor positioned in the sterilization chamber when pressure in the sterilization chamber reaches the first selected pressure level to cause an automated control valve provided on a steam feed pipe for feeding steam to the sterilization chamber to close.

15. The method of claim 11,
the step of automatically feeding steam into the sterilization chamber being accomplished by initiating a signal from a sensor positioned in the sterilization chamber when pressure in the sterilization chamber reaches the second selected pressure level to cause an automated control valve provided on a steam feed pipe for feeding steam into the sterilization chamber to open.

16. The method of claim 11,
said means including an orifice plate provided on the conduit having an orifice sized to permit effective draining of the condensate through the conduit while the sterilization chamber is pressurized without substantial loss of steam pressure in the sterilization chamber.

17. The method of claim 11,
said means including a restriction formed on at least the portion of the conduit creating a cross-section thereat sized to effectively drain condensate through the conduit while the sterilization chamber is pressurized without substantial loss of steam pressure in the sterilization chamber.

18. The method of claim 11,
said means including a cross-section of the at least the portion of the conduit being in a range of one sixteenth of an inch to one quarter of an inch.

\* \* \* \* \*